US009408536B2

(12) United States Patent
Narayan et al.

(10) Patent No.: US 9,408,536 B2
(45) Date of Patent: Aug. 9, 2016

(54) SYSTEM AND METHOD OF IDENTIFYING SOURCES FOR BIOLOGICAL RHYTHMS

(75) Inventors: Sanjiv Narayan, La Jolla, CA (US); Carey Robert Briggs, La Jolla, CA (US)

(73) Assignees: The Regents of the University of California, Oakland, CA (US); Topera, Inc., Menlo Park, CA (US); The United States of America as Represented by the Department of Veterans Affairs, Washington, DC (US)

( * ) Notice: Subject to any disclaimer, the term of this patent is extended or adjusted under 35 U.S.C. 154(b) by 20 days.

(21) Appl. No.: 13/559,868

(22) Filed: Jul. 27, 2012

(65) Prior Publication Data

US 2013/0150740 A1 Jun. 13, 2013

Related U.S. Application Data

(60) Provisional application No. 61/569,132, filed on Dec. 9, 2011.

(51) Int. Cl.
*A61B 5/024* (2006.01)
*A61B 5/00* (2006.01)
*A61B 5/0464* (2006.01)

(52) U.S. Cl.
CPC ............. *A61B 5/002* (2013.01); *A61B 5/02405* (2013.01); *A61B 5/0464* (2013.01)

(58) Field of Classification Search
CPC ..... A61B 5/02; A61B 5/02405; A61B 5/0464
USPC .................................. 600/508–510
See application file for complete search history.

(56) References Cited

U.S. PATENT DOCUMENTS

| 5,121,750 A | 6/1992 | Katims |
| 5,172,699 A | 12/1992 | Svenson et al. |
| 5,433,198 A | 7/1995 | Desai |
| 5,450,846 A | 9/1995 | Goldreyer |
| 5,480,422 A | 1/1996 | Ben-Haim |
| 5,582,173 A | 12/1996 | Li |
| 5,657,755 A | 8/1997 | Desai |
| 5,662,108 A | 9/1997 | Budd et al. |
| 5,687,737 A | 11/1997 | Branham et al. |
| 5,718,241 A | 2/1998 | Ben-Haim et al. |

(Continued)

OTHER PUBLICATIONS

Houben, R.P.M., et al, "Automatic mapping of human atrial fibrillation by template matching", Heart Rhythm, vol. 3, No. 10, Oct. 1, 2006, pp. 1221-1228.
Nademanee, Koonlawee, et al., "A new approach for catheter ablation of atrial fibrillation: mapping of the electrophysiologic substrate", J. Amer.Coll.Cardiol., vol. 43, No. 11, Jun. 2, 2004, pp. 2044-2053.
Narayan, S.M., et al., "Dynamics factors preceding the initiation of atrial fibrillation in humans", Heart Rhythm, vol. 5, No. 6, Jun. 1, 2008, pp. S22-S25.
Ciaccio, Edward J. et al., "Development of Gradient Descent Adaptive Algorithms to Remove Common Mode Artifact for Improvement of Cardiovascular Signal Quality", Annals of Biomedical Engineering, vol. 35, No. 7, Jul. 2007, pp. 1146-1155.

(Continued)

*Primary Examiner* — Michael Kahelin
*Assistant Examiner* — Minh Duc Pham
(74) *Attorney, Agent, or Firm* — Eleanor Musick; Musick Davison LLP

(57) ABSTRACT

An example system and method of locating a source of a heart rhythm disorder are disclosed. In accordance with the method, a first pair of cardiac signals is processed to define a first coefficient associated with variability of the first pair of signals at a first region of the heart. Further, a second pair of cardiac signals is processed to define a second coefficient associated with variability of the second pair of signals at a second region of the heart. Thereafter, the first coefficient of variability is compared to the second coefficient of variability to determine a direction towards the source of the rhythm disorder.

52 Claims, 11 Drawing Sheets
(3 of 11 Drawing Sheet(s) Filed in Color)

(56) References Cited

U.S. PATENT DOCUMENTS

| | | | |
|---|---|---|---|
| 5,795,303 A | 8/1998 | Swanson et al. |
| 5,817,134 A | 10/1998 | Greenhut et al. |
| 5,840,025 A | 11/1998 | Ben-Haim |
| 5,848,972 A | 12/1998 | Triedman et al. |
| 5,868,680 A | 2/1999 | Steiner et al. |
| 5,954,665 A | 9/1999 | Ben-Haim |
| 6,052,618 A | 4/2000 | Dahlke et al. |
| 6,066,094 A | 5/2000 | Ben-Haim |
| 6,115,628 A | 9/2000 | Stadler et al. |
| 6,188,924 B1 | 2/2001 | Swanson et al. |
| 6,236,883 B1 | 5/2001 | Ciaccio et al. |
| 6,301,496 B1 | 10/2001 | Reisfeld |
| 6,360,121 B1 | 3/2002 | Shoda |
| 6,522,905 B2 | 2/2003 | Desai |
| 6,584,345 B2 | 6/2003 | Govari |
| 6,847,839 B2 | 1/2005 | Ciaccio et al. |
| 6,856,830 B2 | 2/2005 | He |
| 6,892,091 B1 | 5/2005 | Ben-Haim et al. |
| 6,920,350 B2 | 7/2005 | Xue et al. |
| 6,941,166 B2 | 9/2005 | MacAdam et al. |
| 6,959,212 B2 | 10/2005 | Hsu et al. |
| 6,975,900 B2 | 12/2005 | Rudy et al. |
| 6,978,168 B2 | 12/2005 | Beatty et al. |
| 7,016,719 B2 | 3/2006 | Rudy et al. |
| 7,043,292 B2 | 5/2006 | Tarjan et al. |
| 7,117,030 B2 | 10/2006 | Berenfeld et al. |
| 7,123,954 B2 | 10/2006 | Narayan et al. |
| 7,206,630 B1 | 4/2007 | Tarler |
| 7,245,962 B2 | 7/2007 | Ciaccio et al. |
| 7,263,397 B2 | 8/2007 | Hauck et al. |
| 7,283,865 B2 | 10/2007 | Noren |
| 7,289,843 B2 | 10/2007 | Beatty et al. |
| 7,328,063 B2 | 2/2008 | Zhang et al. |
| 7,505,810 B2 | 3/2009 | Harlev et al. |
| 7,515,954 B2 | 4/2009 | Harlev et al. |
| 7,751,882 B1 | 7/2010 | Helland |
| 7,761,142 B2 | 7/2010 | Ghanem et al. |
| 7,761,150 B2 | 7/2010 | Ghanem et al. |
| 7,907,994 B2 | 3/2011 | Stolarski et al. |
| 7,930,018 B2 | 4/2011 | Harlev et al. |
| 7,930,020 B2 | 4/2011 | Zhang et al. |
| 8,165,666 B1 | 4/2012 | Briggs et al. |
| 8,165,671 B2 * | 4/2012 | Freeman et al. | 607/5 |
| 8,175,702 B2 | 5/2012 | Efimov et al. |
| 8,521,266 B2 | 8/2013 | Narayan et al. |
| 8,594,777 B2 | 11/2013 | Briggs et al. |
| 8,639,325 B2 | 1/2014 | Efimov et al. |
| 8,676,303 B2 | 3/2014 | Narayan |
| 8,700,140 B2 | 4/2014 | Narayan et al. |
| 8,838,222 B2 | 9/2014 | Narayan et al. |
| 8,838,223 B2 | 9/2014 | Narayan et al. |
| 2002/0010392 A1 | 1/2002 | Desai |
| 2003/0236466 A1 | 12/2003 | Tarjan |
| 2004/0073262 A1 | 4/2004 | Lovett |
| 2005/0148892 A1 | 7/2005 | Desai |
| 2005/0203502 A1 | 9/2005 | Boveja et al. |
| 2006/0084970 A1 | 4/2006 | Beatty et al. |
| 2006/0161206 A1 | 7/2006 | Efimov et al. |
| 2007/0055167 A1 | 3/2007 | Bullinga |
| 2007/0208260 A1 | 9/2007 | Afonso |
| 2007/0299351 A1 | 12/2007 | Harlev et al. |
| 2008/0097539 A1 | 4/2008 | Belalcazar |
| 2008/0109041 A1 | 5/2008 | De Voir |
| 2008/0114258 A1 | 5/2008 | Zhang et al. |
| 2009/0069704 A1 | 3/2009 | MacAdam et al. |
| 2009/0099468 A1 | 4/2009 | Thiagalingam et al. |
| 2009/0112106 A1 * | 4/2009 | Zhang | 600/509 |
| 2009/0177071 A1 | 7/2009 | Harlev et al. |
| 2009/0177072 A1 | 7/2009 | Harlev et al. |
| 2009/0299424 A1 | 12/2009 | Narayan |
| 2010/0094274 A1 | 4/2010 | Narayan |
| 2010/0204592 A1 | 8/2010 | Hatib et al. |
| 2010/0217143 A1 | 8/2010 | Whittington et al. |
| 2010/0249627 A1 | 9/2010 | Zhang |
| 2010/0298729 A1 | 11/2010 | Zhang et al. |
| 2010/0305456 A1 | 12/2010 | Braiinard, II |
| 2011/0087121 A1 | 4/2011 | Zhang et al. |
| 2011/0112425 A1 | 5/2011 | Muhlsteff et al. |
| 2011/0130801 A1 | 6/2011 | Maskara et al. |
| 2011/0196249 A1 | 8/2011 | Staeuber et al. |
| 2011/0251505 A1 | 10/2011 | Narayan |
| 2011/0257547 A1 | 10/2011 | Zhang et al. |
| 2011/0282227 A1 | 11/2011 | Zhang et al. |
| 2012/0232417 A1 | 9/2012 | Zhang et al. |
| 2013/0006131 A1 | 1/2013 | Narayan et al. |
| 2013/0150742 A1 | 6/2013 | Briggs et al. |
| 2013/0226016 A1 | 8/2013 | Narayan et al. |
| 2013/0331718 A1 | 12/2013 | Narayan et al. |
| 2014/0066787 A1 | 3/2014 | Narayan et al. |
| 2014/0073981 A1 | 3/2014 | Narayan et al. |
| 2014/0114204 A1 | 4/2014 | Narayan et al. |
| 2014/0228696 A1 | 8/2014 | Narayan et al. |
| 2014/0276152 A1 | 9/2014 | Narayan et al. |

OTHER PUBLICATIONS

Sornborger, Andrew, et al., "Extraction of Periodic Multivariate Signals: Mapping of Voltage-Dependent Dye Fluorescence in the Mouse Heart", IEEE Transactions on Medical Imaging, vol. 22, No. 12, Dec. 2003, pp. 1537-1549.

Sun, Yan, et al., "Characteristic wave detection in ECG signal using morphological transform", BMC Cardiovascular Disorders, vol. 5, No. 28, 2005.

Tai, Dean C.S., et al., "Correction of motion artifact in transmembrane voltage-sensitive fluorescent dye emission in hearts", Am. J. Physiol. Heart Circ. Physiol., vol. 287, 2004, pp. H985-H993.

PCT/US2012/068639—International Search Report and Written Opinion of the International Searching Authority, Mar. 29, 2013, 9 pages.

Lin, Y-J, et al., "Electrophyiological Characteristics and Catheter Ablation in Patients With Paroxysmal Right Atrial Fibrillation", Circulation, Sep. 20, 2005; 112(12): 1692-1700, EPub Sep. 12, 2005.

Houben, R.P.M., et al., "Processing of Intracardiac Electrograms in Atrial Fibrillation", IEEE Engineering in Medicine and Biology Magazine, Nov./Dec. 2006, pp. 40-51.

Saksena, S., et al., "Regional Endocardial Mapping of Spontaneous and Induced Atrial Fibrillation in Patients With Heart Disease and Refractory Atrial Fibrillation", Am J Cardiol, 1999; 84:880-889.

EP 12711553 Supplementary European Search Report & European Search Opinion, Sep. 11. 2013.

PCT/US2012/029935 International Search Report and Written Opinion, Nov. 8, 2012.

EP 09819953 Supplementary European Search Report & European Search Opinion Feb. 7, 2012.

PCT/US2011/031468 International Preliminary Report on Patentability and Written Opinion, Oct. 9, 2012.

PCT/US2011/031470 International Preliminary Report on Patentability and Written Opinion, Oct. 9, 2012.

PCT/US2009/060178 International Preliminary Report on Patentability and Written Opinion, Apr. 12, 2011.

PCT/US2012/036157 International Preliminary Report on Patentability and Written Opinion, Aug. 14, 2012.

PCT/US12014/029645 International Search Report and Written Opinion, Aug. 18, 2014.

PCT/US2012/068640 International Preliminary Report on Patentability and Written Opinion, Jun. 10, 2013.

PCT/US2014/029616 International Search Report and Written Opinion, Sep. 18, 2014.

* cited by examiner

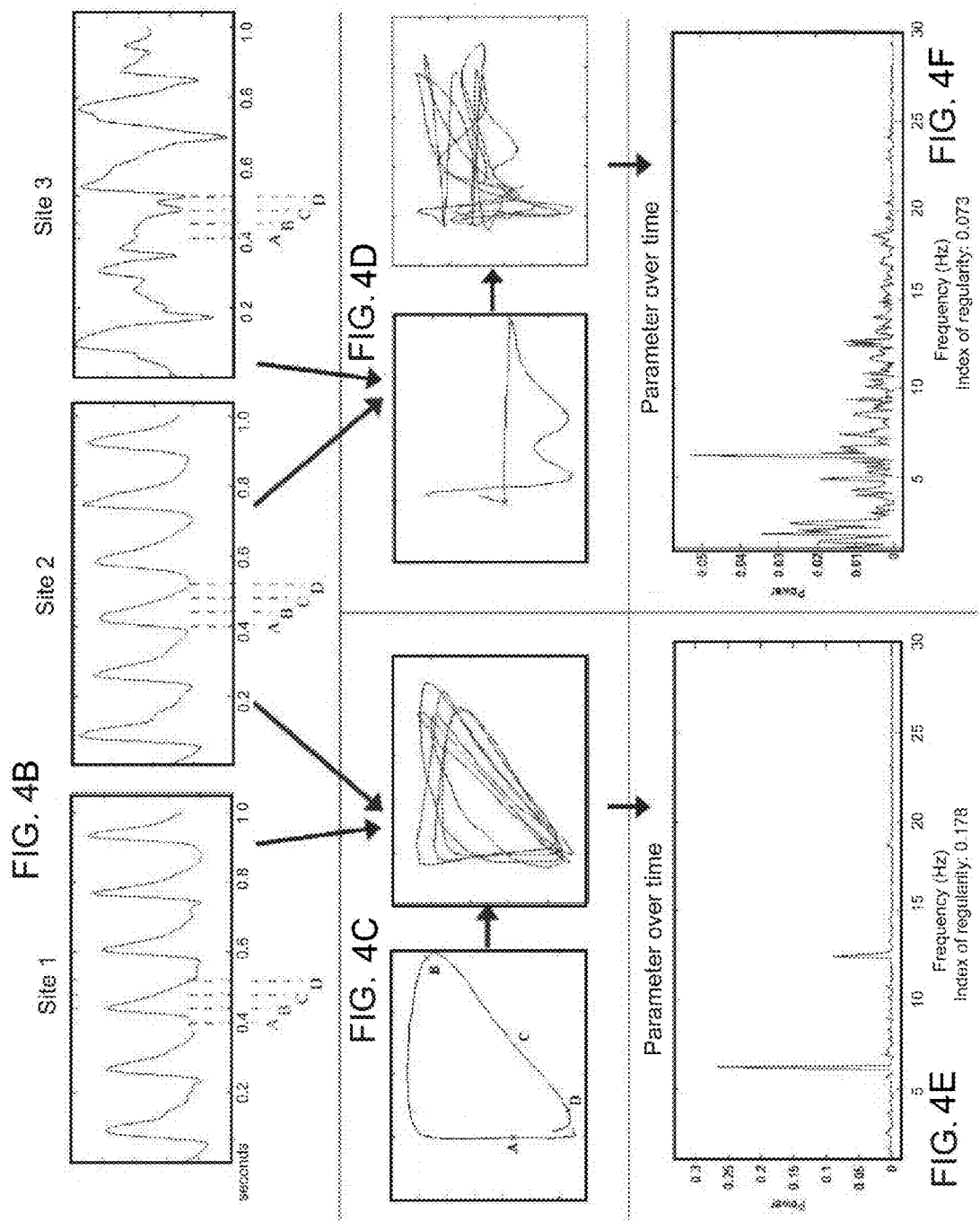

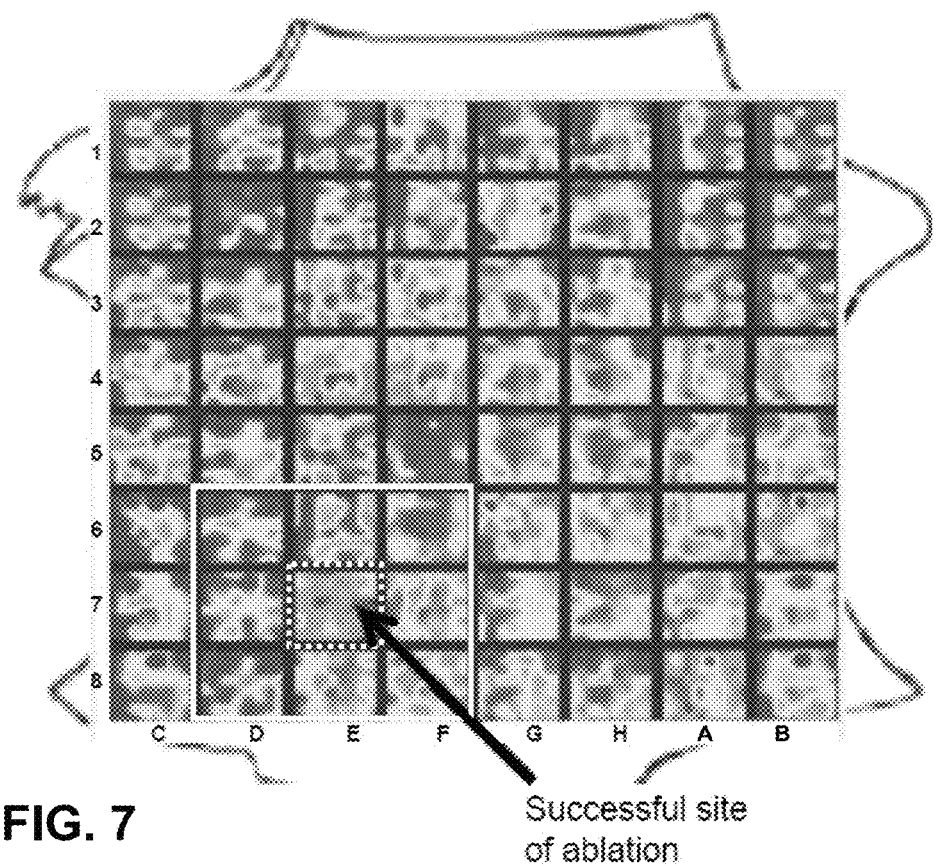
FIG. 7  Successful site of ablation

SYSTEM AND METHOD OF IDENTIFYING SOURCES FOR BIOLOGICAL RHYTHMS

CROSS REFERENCE TO RELATED APPLICATION

This application claims the benefit of U.S. Provisional Application No. 61/569,132 filed on Dec. 9, 2011, the disclosure of which is incorporated herein by reference in its entirety.

FEDERAL GRANT

This invention was made with government support under Grants HL070529 and HL083359 awarded by the National Institutes of Health. The government has certain rights in the invention.

BACKGROUND

1. Field

The present application relates generally to biological rhythm disorders. More specifically, the present application is directed to a system and method of identifying a source (or sources) of a biological rhythm disorder, such as a heart rhythm disorder.

2. Brief Discussion of Related Art

Heart rhythm disorders are common and represent significant causes of morbidity and death throughout the world. Malfunction of the electrical system in the heart represents a proximate cause of heart rhythm disorders. Heart rhythm disorders exist in many forms, of which the most complex and difficult to treat are atrial fibrillation (AF), ventricular tachycardia (VT) and ventricular fibrillation (VF). Other rhythm disorders are more simple to treat, but may also be clinically significant including atrial tachycardia (AT), supraventricular tachycardia (SVT), atrial flutter (AFL), premature atrial complexes/beats (SVE) and premature ventricular complexes/beats (PVC). While under normal conditions the sinus node keeps the heart in sinus rhythm, under certain conditions rapid activation of the normal sinus node can cause inappropriate sinus tachycardia or sinus node reentry, both of which also represent heart rhythm disorders.

Treatment of heart rhythm disorders—particularly complex rhythm disorders of AF, VF and VT—can be very difficult. Pharmacologic therapy for complex rhythm disorder is not optimal. Ablation has been used increasingly in connection with heart rhythm disorders by maneuvering a sensor/probe to the heart through the blood vessels, or directly at surgery, and delivering energy to a location of the heart to mitigate and in some cases to eliminate the heart rhythm disorder. However, in complex rhythm disorders ablation is often difficult and ineffectual because tools that identify and locate a cause (source) of the heart rhythm disorder are poor and hinder attempts to deliver energy to a correct region of the heart to eliminate the disorder.

Certain systems and methods are known for treating simple heart rhythm disorders. In a simple heart rhythm disorder (e.g., atrial tachycardia), the source of the disorder can be identified by tracing activation back to the earliest location, which can be ablated to mitigate and in some cases to eliminate the disorder. However, even in simple heart rhythm disorders, ablating the cause of a heart rhythm disorder is challenging and experienced practitioners often require hours to ablate simple rhythm disorders that show consistent beat-to-beat activation patterns, such as atrial tachycardia.

There are few, if any, known systems and methods that have been successful with respect to identifying the sources or causes for complex rhythm disorders such as AF, VF or polymorphic VT. In a complex rhythm disorder, an earliest location of activation onsets cannot be identified because activation onset patterns change from beat to beat and are often continuous without an earliest or a latest point.

Diagnosing and treating heart rhythm disorders generally involves the introduction of a catheter having a plurality of sensors/probes into the heart through blood vessels of a patient. The sensors detect electric activity of the heart at sensor locations in the heart. The electric activity is generally processed into electrogram signals that represent the activation of the heart at the sensor locations.

In a simple heart rhythm disorder, the signal at each sensor location is generally consistent from beat to beat, enabling identification of the earliest activation. However, in a complex rhythm disorder, the signal at each sensor location from beat to beat may transition between one, several, and multiple deflections of various shapes. For instance, when a signal for a sensor location in AF includes 5, 7, 11 or more deflections, it is difficult if not impossible to identify which deflections in the signal are local to the sensor location in the heart (i.e., local activation onset) versus a nearby sensor location in the heart (i.e., far-field activation onset) or simply noise from another part of the patient's heart, other anatomic structures or external electronic systems. The foregoing deflections make it difficult if not impossible to identify activation onset times of the beats in a signal at a sensor location.

Current strategies in complex rhythm disorders have also considered regularity in signals at sensor locations as a surrogate for the source of the complex rhythm disorder, i.e., the source being more organized at certain sensor locations than at adjacent sensor locations. For example, U.S. Pat. No. 7,117,030 by Berenfeld et al. and U.S. Pat. No. 5,792,189 by Gray et al. exemplify the current approaches in which the source(s) for variable atrial fibrillation (AF) are considered highly regular. However, these approaches have indeed been disappointing in finding the source to treat human atrial fibrillation. As another example, Sanders et al. (Circulation 2005) found that locations of regularity, indicated by high spectral dominant frequency with a high regularity index, were rarely locations where AF terminated by ablation in complex (persistent) AF. Other studies such as Sahadevan (Circulation 2004) identified locations of rapid regular activity in human AF that have never been shown to drive human AF. Animal models (Kalifa, Circulation 2006) and human studies (Nademanee, J Am Coll 2004) suggest that complex fractionated atrial electrograms (CFAE) may form at the junction from regular 'drivers' to variable AF. In clinical use, however, such CFAE sites are poor targets for AF treatment (Oral, Circulation 2007).

There are no known systems and methods that have been able to identify the source (or sources) for a heart rhythm disorder independently of identifying and assigning activation onset times to signals of successive beats. Given the difficulties in identifying the activation onset times, this has significantly limited diagnosis of the source (or sources) of heart rhythm disorders, especially for complex rhythm disorders, and has limited treatment attempts at their elimination.

SUMMARY

The present invention is applicable to identifying sources of various rhythms, including normal and disordered heart rhythms, as well as other biological rhythms and rhythm disorders, such as neurological seizures, esophageal spasms, bladder instability, irritable bowel syndrome, and other biological disorders for which biological signals can be recorded to permit determination, diagnosis, and/or treatment of the cause (or source) of the disorders. The invention does not rely on or calculate the onset of activation in signals at any sensor locations, and thus it is particularly useful in complex rhythm disorders which provide complex activation patterns and complex varying beat signals. It is especially useful in identifying the cause(s) of the disorders of heart rhythm such that they can be treated with expediency.

Complex heart rhythm disorders typically result in an array of activation patterns that are extremely difficult to decipher, so that the ability to determine accurate activation of a heart beat has previously not been possible. Among the advantages of the present invention is the ability to identify a source of a complex rhythm disorder from variability in signals at sensor locations relative to regularity in signals at adjacent sensor locations, independently of the assignment of specific activation onset times (identifying beats) in signals at these sensor locations. In this way, the invention enables a determination of a source (or sources) of the heart rhythm disorder for treatment. Another advantage is that the present invention provides a method and system which can be carried out rapidly while a sensing device—such as a catheter having sensors thereon—is used in or near the patient and is followed by treatment of cardiac tissue to ameliorate the disorder and in many cases to cure the disorder. Treatment may thus occur immediately, since the invention will provide the location(s) of the source of the heart rhythm disorder.

Prior methods and systems suffered from the inability to determine the source of rhythm disorders and consequently provided no means of targeting the source for meaningful and curative treatment. Additionally, prior methods and systems required numerous and complex steps of treatment and yet still failed to provide a means of determining the source(s) of heart rhythm disorders. In contrast, the present invention provides a relatively few number of steps to determine the source(s) for a heart rhythm disorder, including complex rhythm disorders of atrial and ventricular fibrillation.

In accordance with an embodiment, a method of locating a source of a rhythm disorder of a heart is disclosed. In accordance with the method, a first pair of cardiac signals is processed to define a first coefficient associated with variability of the first pair of signals at a first region of the heart. Further, a second pair of cardiac signals is processed to define a second coefficient associated with variability of the second pair of signals at a second region of the heart. Thereafter, the first coefficient of variability is compared to the second coefficient of variability to determine a direction towards the source of the rhythm disorder.

In accordance with another embodiment, a method of locating a source of a rhythm disorder of a heart is disclosed. The method includes processing a first cardiac signal at one or more first time points against a second cardiac signal at one or more second time points to define a first coefficient associated with variability of one or more coordinate pairs of the first cardiac signal against the second cardiac signal. The method further includes processing a third cardiac signal at one or more third time points against a fourth cardiac signal at one or more fourth time points to define a second coefficient associated with variability of one or more coordinate pairs of the third cardiac signal against the fourth cardiac signal. Thereafter, a direction towards the source of the rhythm disorder is determined as being from a lower coefficient of variability to a higher coefficient of variability.

In accordance with a further embodiment, a system to locate a source of a rhythm disorder of a heart is disclosed. The system includes at least one computing device that is configured to process a first pair of cardiac signals to define a first coefficient associated with variability of the first pair of signals at a first region of the heart, process a second pair of cardiac signals to define a second coefficient associated with variability of the second pair of signals at a second region of the heart, and compare the first coefficient of variability to the second coefficient of variability to determine a direction towards the source of the rhythm disorder.

In accordance with yet another embodiment, a system to locate a source of a rhythm disorder of a heart is disclosed. The system includes at least one computing device configured to process a first cardiac signal at one or more first time points against a second cardiac signal at one or more second time points to define a first coefficient associated with variability of one or more coordinate pairs of the first cardiac signal against the second cardiac signal, process a third cardiac signal at one or more third time points against a fourth cardiac signal at one or more fourth time points to define a second coefficient associated with variability of one or more coordinate pairs of the third cardiac signal against the fourth cardiac signal, and determine a direction towards the source of the rhythm disorder being from a lower coefficient of variability to a higher coefficient of variability.

In accordance with another embodiment, a method of treating a cardiac rhythm disorder is disclosed. In accordance with the method, pairs of cardiac signals are iteratively selected from a plurality of cardiac signals. Each pair has a first cardiac signal and different second cardiac signal. The first cardiac signal at a plurality of first time points is processed against the different second cardiac signal at a plurality of second time points to define a plurality of coordinate pairs of the first cardiac signal against the different second cardiac signal for each selected pair. A coefficient of variability that exceeds a threshold is determined. The coefficient of variability can be computed from the plurality of coordinate pairs among the first cardiac signal and the second cardiac signal each selected pair.

Thereafter, a matrix of coefficients of variability is constructed for each selected pair. The matrixes of coefficients are organized for the iteratively selected pairs in relation to each other. One or more sources of the cardiac rhythm disorder are located using the organized matrixes of coefficients. Treatment is delivered to cardiac tissue at the one or more sources to suppress or eliminate the cardiac rhythm disorder.

These and other purposes, goals and advantages of the present application will become apparent from the following detailed description of example embodiments read in connection with the accompanying drawings.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

Some embodiments are illustrated by way of example and not limitation in the figures of the accompanying drawings in which:

FIG. 4B illustrates an example method of identifying a source of a heart rhythm disorder as being in a direction from regular activity (low variability) in signals of certain sensor locations toward irregular activity (high variability) in signals of adjacent senor locations in the heart illustrated in FIG. 1;

FIG. 7 illustrates an example plot of indexes of periodic repeating activity (regularity) to identify a source of heart rhythm disorder.

DETAILED DESCRIPTION

A system and method for identifying the sources of heart rhythm disorders are disclosed herein. In the following description, for the purposes of explanation, numerous specific details are set forth in order to provide a thorough understanding of example embodiments. It will be evident, however, to one skilled in the art, that an example embodiment may be practiced without all of the disclosed specific details.

Figure 1:
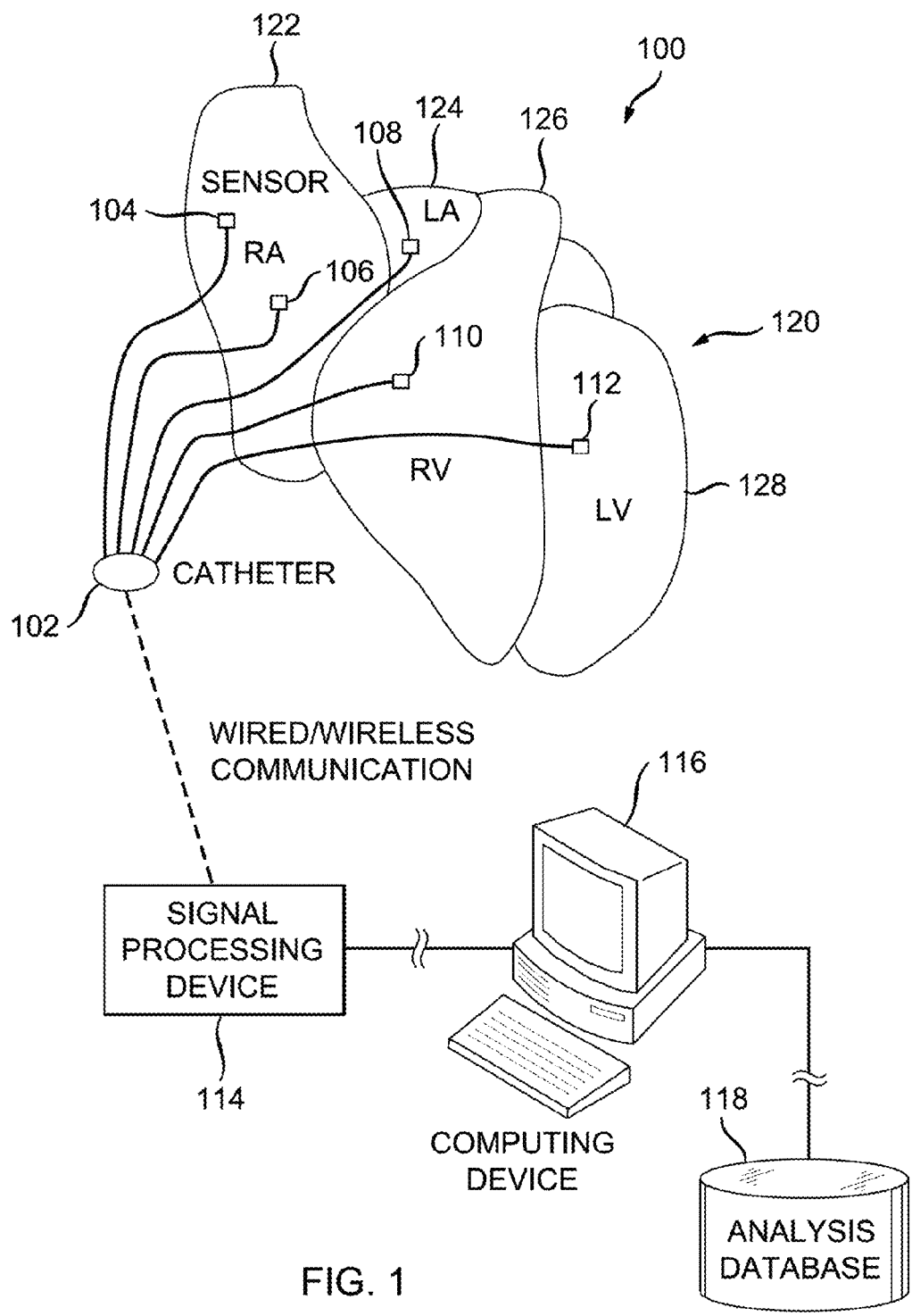
FIG. 1 illustrates an example system to identify a source (or sources) of a heart rhythm disorder.

FIG. 1 illustrates an example system 100 to identify a source (or sources) of a heart rhythm disorder. Specifically, the example system 100 is configured to detect cardiac information (signals) collected/detected from a patient's heart 120 in connection with a heart rhythm disorder. The system 100 is further configured to process the signals in order to determine a region (or multiple regions) of tissue in the patient's heart 120 associated with a degree of regularity (e.g., lower regularity), which differs from a degree of regularity (e.g., higher regularity) of a plurality of adjacent regions of tissue in the patient's heart. For example, the region (or multiple regions) determined to have high variability (low regularity) surrounded by low variability (high regularity) indicates a source(s) of the heart rhythm disorder. The heart 120 includes a right atrium 122, left atrium 124, right ventricle 126 and left ventricle 128.

The example system 100 includes a catheter 102, signal processing device 114, computing device 116 and analysis database 118.

The catheter 102 is configured to detect cardiac activation information in the heart and to transmit the detected cardiac activation information to the signal processing device 114, via a wireless connection, wired connection, or a combination of both wired and wireless connections. The catheter includes a plurality of probes/sensors 104-112, which can be inserted into the heart through the patient's blood vessels.

In some embodiments, one or more of the sensors 104-112 may not be inserted into the patient's heart. For example, some sensors may detect cardiac activation via the patient's surface (e.g., electrocardiogram—ECG) or remotely without contact with the patient (e.g., magnetocardiogram). As another example, some sensors may also derive cardiac activation information from cardiac motion of a non-electrical sensing device (e.g., echocardiogram). In various embodiments, these sensors can be used separately or in different combinations, and further these separate or different combinations can also be used in combination with sensors inserted into the patient's heart.

The sensors 104-112, which are positioned at sensor locations in the heart under consideration, can detect cardiac activation information at the sensor locations and can further deliver energy to ablate the heart at the sensor locations. It is noted that the sensors 104-112 can also detect cardiac activation information from overlapping regions of the heart (e.g., right atrium 122 and left atrium 124).

The signal processing device 114 is configured to process (e.g., clarify and amplify) the cardiac activation information detected by the sensors 104-112 at the sensor locations into electrogram signals and to provide the processed signals to the computing device 116 for analysis in accordance with methods disclosed herein. In processing the cardiac activation information from the sensors 104-112, the signal processing device 114 can subtract cardiac activation information from overlapping regions of the heart 120 to provide processed signals to the computing device 116 for analysis. While in some embodiments, the signal processing device 114 is configured to provide unipolar signals, in other embodiments, the signal processing device 114 can provide bipolar signals.

The computing device 116 is configured to receive detected/processed signals from the signal processing device 114 and further configured to analyze the signals in accordance with methods disclosed herein to determine degree of regularity (or degree variability) in adjacent regions of the patient's heart, such that it is possible to generate a map(s) (representation(s)) of regularity (or variability) of the adjacent regions that can be used to locate a source(s) of the heart rhythm disorder and to eliminate the source(s).

The analysis database 118 is configured to support or aid in the analysis of the signals by the computing device 116. In some embodiments, the analysis database 118 can store the map of regularity associated with or generated on the basis of signals at a plurality of adjacent sensor locations over a period of time, as will be described in greater detail herein. The analysis database 118 can also provide storage of intermediate data associated with the map of regularity.

Figure 2:
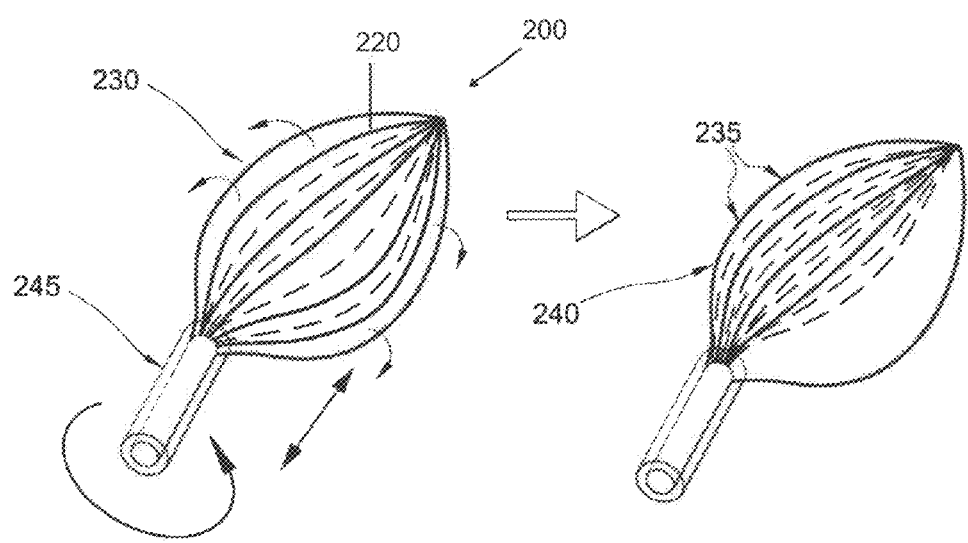
FIG. 2 illustrates an example catheter that can be used to identify the source of a heart rhythm disorder in FIG. 1.

FIG. 2 illustrates an example catheter 200 to detect electrical signals via a plurality of sensors 240 at sensor locations in the heart 120 under consideration. Catheter 200 can be similar to or different than catheter 102 and sensors 240 can be similar to or different than sensors 104-112 in FIG. 1.

The catheter 200 includes multiple splines (or meridians) 220 each of which can include multiple sensors (or probes) 240. By rotating along a shaft axis 245, the splines or meridians 220 may be spaced or separated more widely spatially as depicted at 230 or spaced more closely spatially as depicted at 235.

Different spatial arrangements of the sensors 240 (via spatial separation of the splines 220) can have the effect of spatially extending the area of the heart 120 under consideration. The sensors 240 positioned in a spatial arrangement at sensor locations of the heart 120 under consideration can detect cardiac electrical signals at the sensor locations and can further deliver energy to ablate (or other treatment to treat) the heart at the sensor locations.

Different catheters with various spatial arrangements of the sensors 240 can be used, such as spiral, radial spokes or other spatial arrangements.

Figure 3A:
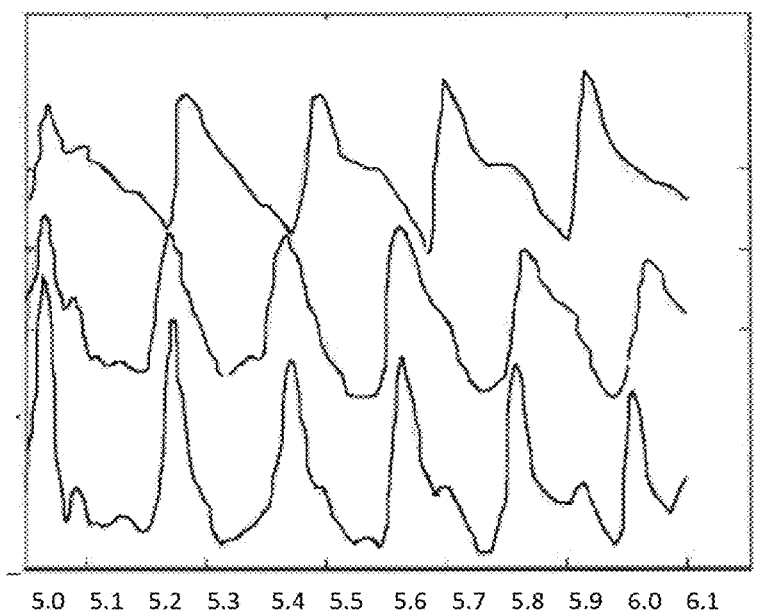
FIGS. 3A-B illustrate an example simple electrogram signal of a heart rhythm disorder and a complex electrogram signal of a heart rhythm disorder from sensors positioned at sensor locations in a heart illustrated in FIG. 1.

FIG. 3A illustrates an example of simple electrocardiogram signals of a heart rhythm disorder from sensors positioned at sensor locations in the heart 120.

As an example, the heart rhythm disorder can be a complex rhythm disorder AF, VF and polymorphic VT, or another heart rhythm disorder. In this example, the signals generally show identifiable activation onsets (e.g., for heart beats). The heart beats can be characterized by an activation onset with a sharp inflection point and high slope representing depolarization, followed by a period of gentle, low-deviation slope representing repolarization, typically lasting between about 100 ms and 250 ms.

The regularity or phase relationship between the simple signals in FIG. 3(A) is generally easily identifiable.

Figure 3B:
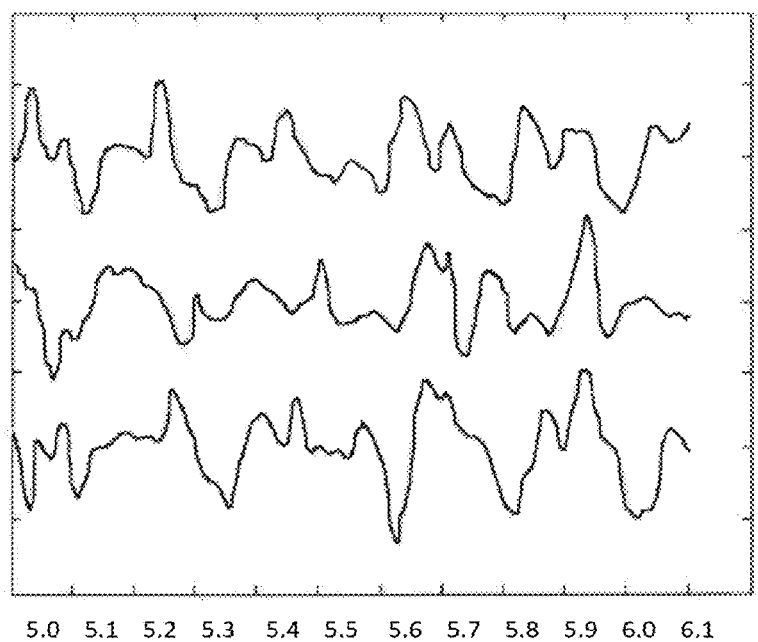

FIG. 3B illustrates an example of complex electrocardiogram signals of a heart rhythm disorder from sensors positioned at sensor locations in the heart 120. As an example, the heart rhythm disorder can be a complex rhythm disorder AF, VF and polymorphic VT, or another heart rhythm disorder.

The signals in FIG. 3(B) do not generally show identifiable activation onsets (e.g., for heart beats). The signals include multiple deflections of short duration caused by the heart rhythm disorder that makes the discernment of activation onsets (depolarization) prohibitively difficult. Similarly, regularity or phase relationship between complex signals in FIG. 3(B) is not easily discerned.

Figure 4A:
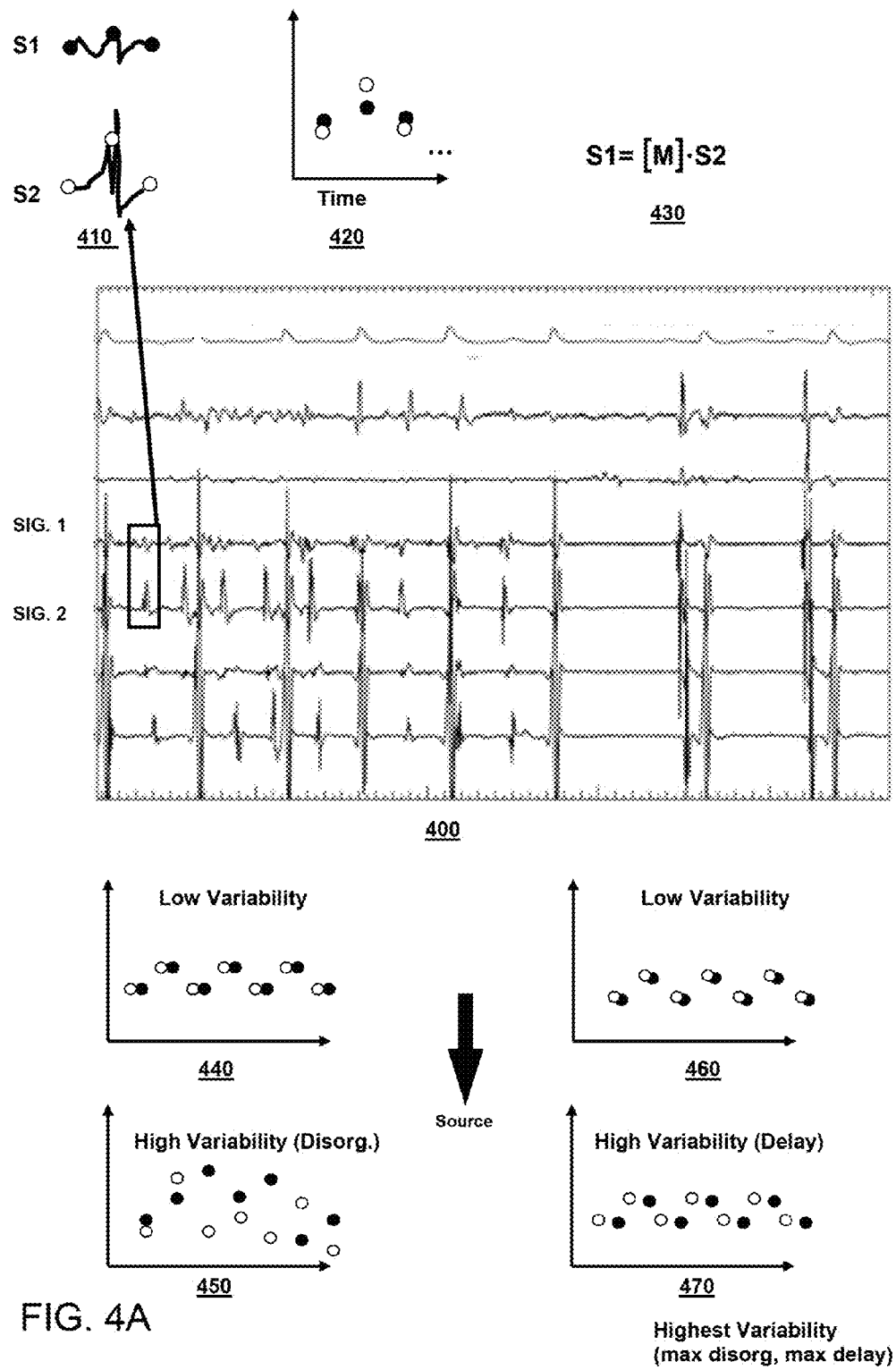
FIG. 4A illustrates an example method of identifying a source of a heart rhythm disorder as being in a direction from regular activity (low variability) in signals of certain sensor locations toward irregular activity (high variability) in signals of adjacent senor locations in the heart illustrated in FIG. 1.

FIG. 4A illustrates an example method of identifying a source of a heart rhythm disorder as being in a direction from regular activity (low variability) in signals of certain sensor locations toward irregular activity (high variability) in signals of adjacent senor locations in the heart 120 illustrated in FIG. 1.

Panel 400 illustrates a plurality of example signals (e.g., ECG signals) obtained from adjacent sensor locations (e.g., different regions) in the heart 120 of FIG. 1, such as via electrodes in the catheter 102, 200. To illustrate the example method, a pair of signals (e.g., two (2) example signals) is selected from sensor locations, denoted as SIG. 1 and SIG 2. It is noted that multiple different signals can be considered from the catheter 102, 200, e.g., 64, 128, or another number of signals. Each of the signals in the pair is a voltage time series. The signals have varying amplitudes (e.g., voltage) along the signals as detected by the sensors of the catheter 102, 200. A multiplicity of time points along each of the example signals SIG. 1, SIG. 2 can be identified or selected in accordance with the example methods disclosed herein.

As shown in panel 410, one or more time points are selected in SIG. 1 and corresponding (e.g., contemporaneous) one or more time points are selected in SIG. 2. These corresponding time points in SIG. 1, SIG. 2 are grouped (e.g., paired) into one or more coordinate pairs of this signal pair. For example, panel 420 shows graphically such grouping of the time points among signal pair SIG. 1, SIG. 2. A coefficient of variability is defined or determined for the one or more coordinate pairs. In one example shown in panel 430, the coefficient of variability for these coordinate pairs in the signal pair can be defined from a transformation matrix M that transforms the time points of SIG. 1 to time points of SIG. 2. For example, the values in the matrix M can averaged to define the coefficient of variability. Other evaluation techniques can be used, such as standard deviation analysis, frequency analysis, entropy analysis, cross-correlation analysis, randomness analysis, Monte Carlo simulation methods, quantification of chaos and/or other complex statistical analyses, as well as combinations thereof.

The processing described in panels 400-430 can be repeated for different pairs of signals shown in panel 400. It is reiterated that multiple different signals can be considered from the catheter 102, 200, e.g., 64, 128, or another number of signals. For example, one or more time points can be selected in a SIG. 3 (not shown) and corresponding (e.g., contemporaneous) one or more time points are selected in a SIG. 4 (not shown), which can be a second signal pair SIG. 3, SIG. 4. In some embodiments, SIG. 3 can be SIG. 1, e.g., a common signal among the first pair of signals and the second pair of signals. In other embodiments, both signals can be different among the different signal pairs. The corresponding time points in SIG. 3, SIG. 4 are grouped (e.g., paired) into one or more coordinate pairs. A coefficient of variability is defined or determined for the one or more coordinate pairs of the second signal pair SIG. 3, SIG. 4, similarly or differently that described above in the first signal pair SIG 1, SIG 2.

Thereafter, the source of the disorder can be determined as being in the direction from the lower coefficients of variability (regular) toward the higher coefficients of variability (irregular) among the different signal pairs processed. For example, as shown in panel 440, a first signal pair can have a low coefficient of variability. In other words, signals in the first signal pair can be regular, e.g., not disorganized in amplitude (voltage) and time. As shown in panel 450, a second signal pair can have a high coefficient of variability. In other words, signals in the second signal pair can be irregular or of higher variability than the signals in the first signal pair, e.g., disorganized in amplitude (voltage) and/or time. Accordingly, the source of complex rhythm disorder lies in the direction of higher variability.

As another example, as shown in panel 460, a third signal pair can have a low coefficient of variability. In other words, signals in the third signal pair can be regular, e.g., not disorganized in amplitude (voltage) and time. As shown in panel 470, a fourth signal pair can have a high coefficient of variability. In other words, signals in the fourth signal pair can be irregular or of higher variability than the signals in the third signal pair, e.g., disorganized in amplitude (voltage) and/or time (offset). Accordingly, the source of complex rhythm disorder lies in the direction of higher variability. For example, the highest variability among the different signal pairs of panel 400 would be represented by a maximum disorganization (variability) in amplitude and a maximum disorganization (variability) in delay.

FIG. 4B illustrates an example method of identifying a source of a heart rhythm disorder as being in a direction from regular activity (low variability) in signals of certain sensor locations toward irregular activity (high variability) in signals of adjacent senor locations in the heart 120 illustrated in FIG. 1.

Panel (A) illustrates three (3) example signals (e.g., ECG signals) obtained from three adjacent sensor locations (sites 1, 2 and 3) in the heart 120 of FIG. 1, such as via electrodes in the catheter 102, 200. For the following processing example, signals from sites 1 and 2 can be considered a first signal pair, while sites 2 and 3 can be considered a second signal pair, where the signal from site 2 is common among signal pairs. It is reiterated that multiple signals can be considered from the catheter 102, 200, e.g., 64, 128, or another number of signals. Each of the signals is a voltage time series. The three signals have varying amplitudes (e.g., voltage) along the signals as detected by the sensors of the catheter 102, 200. Four example time points (A, B, C and D) are illustrated in the signals for clarity and brevity in describing the processing of the signals in accordance with the example method as described below. However, it is to be noted that there is a multiplicity of time points along each of the example signals that can be processed in accordance with the example methods disclosed herein.

In accordance with the example method, a derivative of each signal can be determined at the plurality of selected time points. The derivative can be a zero order derivative or a higher-order derivative (e.g., a first-order derivative or second-order derivative). For example, a derivative of the first (analysis) cardiac signal determined at a plurality of first time points (e.g., A, B, C and D). As another example, a derivative of the second (reference) cardiac signal can be determined at a plurality of second time points (e.g., A, B, C and D). Similarly, a derivative of the third cardiac signal is determined at a plurality of third time points (e.g., A, B, C and D). In some embodiments, the pluralities of time points in the different signals are contemporaneous. It is again noted that the signals include a multiplicity of time points that can be processed in accordance with the example methods as described herein.

In panel (B), the derivative of the first (analysis) cardiac signal at the plurality of first time points can be processed against the derivative of the second (reference) cardiac signal at the plurality of second time points to define a plurality of coordinate pairs of the first cardiac signal against the second cardiac signal in the first signal pair. These coordinate pairs can be maintained in memory and/or saved to database 118. In some embodiments, the plurality of coordinate pairs associated with processing of the first cardiac signal against the second cardiac signal can be plotted and connected to generate a plurality of loops. For example, the coordinate pairs associated with example time points A-D can be plotted and connected to generate a first loop, as shown in a left part of panel (B).

Further with reference to panel (B), the plotting and connecting can be repeated for a plurality of first and second time points to generate multiple loops as shown in a right part of panel (B). In this example, a single loop is shown in a left part of panel (B) based on time points A-D for illustrative purposes. The single loop can represent a single cycle of a heart rhythm, while multiple loops can represent multiple cycles of the heart rhythm. As illustrated in the right part of panel (B), a high degree of regularity (e.g., low degree of variability) is observed among the loops in the right part of panel (B). It is noted that the same processing can be repeated for the first (analysis) cardiac signal against different second (reference) cardiac signals, i.e., others of the adjacent 64 or 128 signals.

In panel (C), the derivative of the second (analysis) cardiac signal at the plurality of first time points can be processed against the derivative of the third (reference) cardiac signal at the plurality of third time points to define a plurality of coordinate pairs of the second cardiac signal against the third cardiac signal in the second signal pair. These coordinate pairs can be maintained in memory and/or saved to database 118. In some embodiments, the plurality of coordinate pairs associated with processing of the second cardiac signal against the third cardiac signal can be plotted and connected to generate a plurality of loops. It is noted that the same processing can be repeated for the second (analysis) cardiac signal against different third (reference) cardiac signals, i.e., others of the adjacent 64 or 128 signals.

Further with reference to panel (C), the plotting and connecting can be repeated for a plurality of second and third time points to generate multiple loops as shown in a right part of panel (C). In this example, a single loop is shown in a left part of panel (C) based on time points A-D for illustrative purposes. The single loop can represent a single cycle of a heart rhythm, while multiple loops can represent multiple cycles of the heart rhythm. As illustrated in the right part of panel (C), a low degree of regularity (high degree of variability) is observed amongst the loops in the right part of panel (C).

In panel (D), an index of regularity can be determined with respect to the first cardiac signal (analysis signal) against the second (reference) cardiac signal in the first signal pair. An index of variability can be determined instead of the index of regularity. In some embodiments, the index of variability is the inverse of the index of regularity. The high index of regularity (or low index of variability) indicates an approximate congruence (e.g., mathematical congruence) of the plurality of coordinate pairs between the first cardiac signal and the second cardiac signal. The index of regularity (index of variability) can be determined in one of a time domain, frequency domain and spatial domain. Various other methods described herein can also be used. A further determination can be made as to whether the index of regularity of panel (D) exceeds a threshold. In some embodiments, the threshold can be defined to indicate an upper percentile (e.g., top $5^{th}$ percentile) of all indexes of regularity of the first (analysis) cardiac signal against second (reference) cardiac signals, i.e., the adjacent eight (8) signals, repeated for signals from 64 or 128 sensor locations. A different percentile can be used, e.g., $10^{th}$ percentile, or anther percentile number. Similarly, various percentiles can be defined for the coefficients of variability, e.g., top $5^{th}$ or $10^{th}$ percentile of variability.

With reference to the frequency domain, a frequency analysis (e.g., Fourier analysis) can be performed using a selected parameter associated with the plurality of coordinate pairs (or loops) to generate a frequency spectrum, as shown in panel (D). The selected parameter can be amplitude (e.g., voltage), angle, vector, area and derivative. Thereafter, at least one peak is determined in the frequency spectrum of panel (D). In some embodiments, the at least one peak can include a fundamental frequency. In other embodiments, the at least one peak can include the fundamental frequency and also one or more harmonics of the fundamental frequency. In still other embodiments, the at least one peak can include only one or more of the harmonics of the fundamental frequency, i.e., the fundamental frequency can be excluded.

In performing the frequency analysis, a sum of the area of the at least one peak in the frequency spectrum in panel (D) can be calculated. A result (e.g., index of regularity) can be calculated by dividing the sum of the area of the at least one peak by a total area of the frequency spectrum within a predefined frequency range, such as between about 4 Hz and about 12 Hz. In some embodiments, other frequency ranges can be defined. It can be determined whether the result (index of regularity) exceeds the threshold, such as an upper percentile (e.g., top $5^{th}$ percentile) of all indexes of regularity of the first (analysis) cardiac signal against second (reference) cardiac signals, i.e., the adjacent eight (8) signals, repeated for signals from 64 or 128 sensor locations. For example, the index of regularity for the coordinate pairs of panel (B) as shown in panel (D) is 0.178, indicating a high degree of regularity of the first cardiac signal against the second cardiac signal in the first signal pair. In frequency analysis, the index of regularity can be in a range between about 0.0 and about 1.0. An index of variability can be represented as the inverse of the index of regularity, or can be calculated using other computational methods described herein. Similarly, various percentiles can be defined for the index or coefficient of variability.

In panel (E), an index of regularity is determined with respect to the second (analysis) cardiac signal against the third (reference) cardiac signal in the second signal pair. An index or coefficient of variability can be determined instead of the index of regularity. In some embodiments, the index of variability is the inverse of the index of regularity. The high index of regularity (or low index of variability) indicates an approximate congruence (e.g., mathematical congruence) of the plurality of coordinate pairs between the second cardiac signal and the third cardiac signal. As described previously, the index of regularity (index of variability) can be determined in one of a time domain, frequency domain and spatial domain. Various method described herein can be used. A further determination can be made as to whether the index of regularity of panel (E) exceeds a threshold. In some embodiments, the threshold indicates an upper percentile (e.g., top $5^{th}$ percentile) of all indexes of regularity of the second (analysis) cardiac signal against third (reference) cardiac signals, i.e., the adjacent eight (8) signals, repeated for signals from 64 or 128 sensor locations. A different percentile can be used, e.g., $10^{th}$ percentile, or anther percentile number. Similarly, various percentiles can also be defined for the coefficients of variability, e.g., top $5^{th}$ or $10^{th}$ percentile of variability.

Moreover, a frequency analysis (e.g., Fourier analysis) can be performed using a selected parameter associated with the plurality of coordinate pairs to generate a frequency spectrum, as shown in panel (E). The selected parameter can be amplitude (e.g., voltage), angle, vector, area and derivative. Thereafter, at least one peak can be determined in the frequency spectrum of panel (E). In some embodiments, the at least one peak can include a fundamental frequency. In other embodiments, the at least one peak can include the fundamental frequency and also one or more harmonics of the fundamental frequency. In still other embodiments, the at least one peak can include only one or more of the harmonics of the fundamental frequency, i.e., the fundamental frequency can be excluded.

In performing the frequency analysis, a sum of the area of the at least one peak in the frequency spectrum of panel (E) can be calculated. A result (i.e., index of regularity) can be calculated by dividing the sum of the area of the at least one peak by a total area of the frequency spectrum within a predefined frequency range, such as between about 4 Hz and about 12 Hz. In some embodiments, other frequency ranges can be defined. It can be determined whether the result (index of regularity) exceeds the threshold, e.g., an upper percentile (e.g., top $5^{th}$ percentile) of all indexes of regularity of the first (analysis) cardiac signal against second (reference) cardiac signals, i.e., the adjacent eight (8) signals, repeated for signals from 64 or 128 sensor locations. For example, the index of regularity for the coordinate pairs of panel (C) as shown in panel (E) is 0.073, indicating a low degree of regularity of the second cardiac signal against the third cardiac signal. An index of variability can be represented as the inverse of the index of regularity, or can be calculated using other computational methods described herein. Similarly, various percentiles can be defined for the index of variability.

As shown in panels (B) and (D), the first signal pair can have a low coefficient of variability (high index of regularity). In other words, the signals in the first signal pair can be regular, e.g., not disorganized in amplitude (voltage) and time. As shown in panels (C) and (E), the second signal pair can have a high coefficient of variability (low index of regularity). In other words, the signals in the second signal pair can be irregular or of higher variability than the signals in the first signal pair, e.g., disorganized in amplitude (voltage) and/or time (offset). Accordingly, it can be determined that the source of complex rhythm disorder lies in the direction of higher variability, from the first pair in the direction of the second signal pair.

Figure 5:
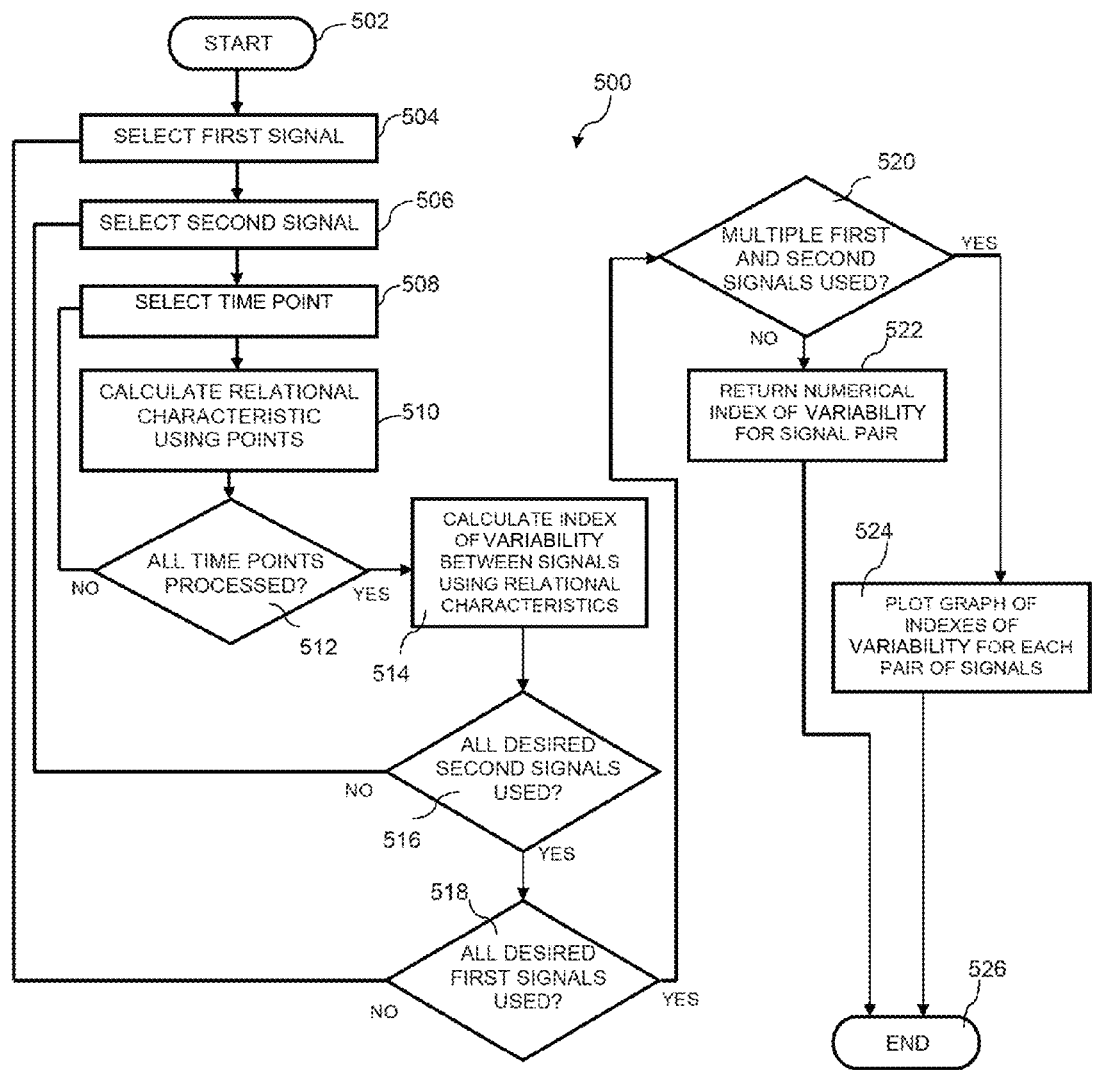
FIG. 5 is a flowchart that illustrates an example method of determining periodic repeating activity and/or variability to identify a source of a heart rhythm disorder.

FIG. 5 is a flowchart that illustrates an example method 500 of determining periodic repeating activity and/or variability to identify a source of a heart rhythm disorder. The method starts at operation 502. At operations 504, 506, a pair of cardiac signals is selected form a plurality of cardiac signals, representing a signal pair. Specifically, at operation 504 a first (analysis) signal is selected from the plurality of signals and at operation 506 a second different (reference) signal is selected from the plurality of signals. As described herein, there can be 64, 128, or another number of signals. The signals can be ECG signals processed via signal processing device 114 of FIG. 1.

At operation 508, a time point is selected with reference to the processing of the first cardiac signal with respect to the second cardiac signal for the selected signal pair. At operation 510, a relational characteristic(s) can be calculated using the time point. This characteristic(s) can be stored, such as in database 118. The characteristic(s) can identify the relationship between the time points. In some embodiments, a derivative of each signal can be determined at the selected time point. Specifically, a derivative of the first cardiac signal can be processed against a derivative of the second cardiac signal at the selected time point to define a coordinate pair of the first cardiac signal against the second cardiac signal for the selected signal pair.

At operation 512, a determination is made as to whether all time points have been processed for the selected signal pair. If it is determined that all time point have not been processed, the method continues to perform operations 508-512 until all time points have been processed. If it is determined that all time point have been processed, the method 500 continues at operation 514.

At operation 514, an index or coefficient of variability (or index of regularity) is computed between the signals in the selected signal pair, for example, using the relational characteristic(s). Various techniques described herein can be used, such as standard deviation analysis, frequency analysis, entropy analysis, cross-correlation analysis, randomness analysis, Monte Carlo simulation methods, quantification of chaos and/or other complex statistical analyses, as well as various combinations thereof. At operation 516, it is determined whether all desired second (reference) signals have been used in relation to the selected first (analysis) signal. If it is determined that all desired second signals have not been used, the method 500 continues at operations 506-516 until all desired second signals have been used in relation to the first selected signal. In some embodiments, the coordinate pairs associated with processing of the first (analysis) cardiac signal against all the second (reference) cardiac signals for different signal pairs at the plurality of time points can be plotted and connected to generate a plurality of loops, as shown in FIG. 4. In other embodiments, coefficients of variability (or indexes of regularity) can be stored as a matrix (e.g., in database 118).

If it is determined that all desired second signals have been processed, the method 500 continues at operation 518 where it is determined whether all desired first (analysis) signals have been used. If it is determined that all desired first signals have not been used, the method 500 continues at operations 504-516 until all desired first signals have been used.

At operation 520, it is determined whether multiple first and multiple second signals were used. If it is determined that multiple signals were not used, then at operation 522 a coefficient of variability (or an index of regularity) can be returned for the selected first and second signals, i.e., the selected signal pair. However, if it is determined that multiple first signals and multiple second signals were used (i.e., multiple signal pairs), then at operation 524 the matrix of coefficients of variability (or matrix of indexes of regularity) can be plotted for each signal pair of first and second signals. (See the plot in FIG. 7). In some embodiments, the coefficients of variability (or indexes of regularity) can be maintained in memory and/or stored in database 118. The one or more coefficients of variability (indexes of regularity) that exceed one or more thresholds can be indicated or identified using different colors as will be described herein in reference to FIGS. 6 and 7. As described herein, a threshold can be used to indicate an upper percentile (e.g., top $5^{th}$ percentile) of coefficients of variability (or indexes of regularity). The method ends at operation 526.

Figure 6A:
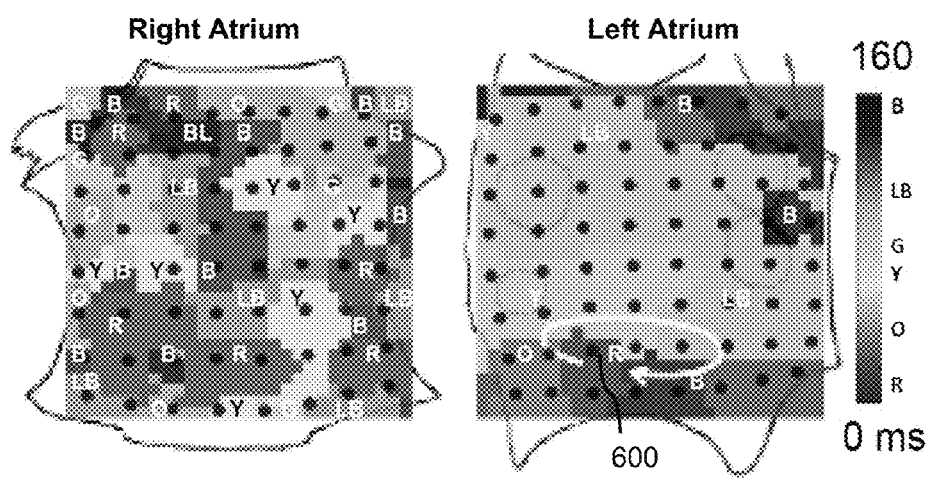
FIG. 6 illustrates example migration of a source (locus) of a heart rhythm disorder and the use of coefficients of variability (or indexes of regularity) to identify such a source of heart rhythm disorder.
Figure 6B:
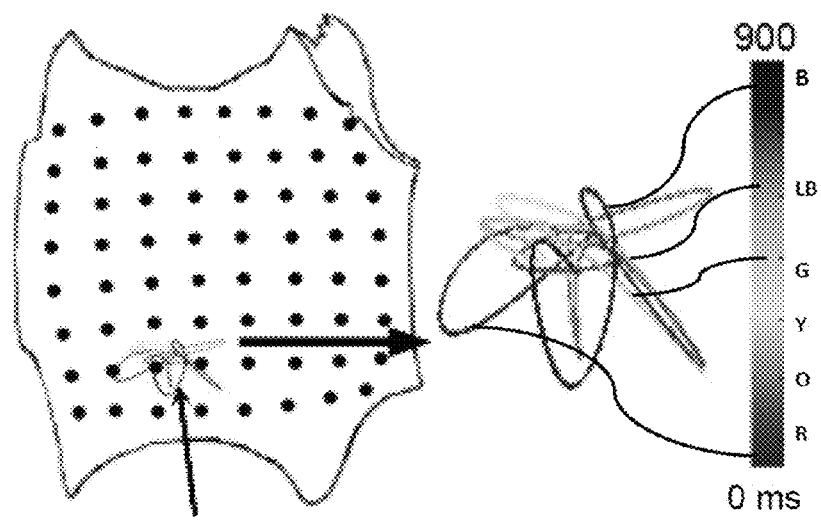

FIGS. 6A-6E illustrate example migration of a source (locus) of a heart rhythm disorder and the use of coefficients of variability (indexes of regularity) to identify such a source of heart rhythm disorder in a patient. Specifically, FIGS. 6A-6E show atrial fibrillation (AF), with termination purely by ablation at the source of the AF as identified by the coefficients of variability (indexes of regularity). In FIG. 6A, left atrial rotational source during AF is traditionally visualized using contours of activation time (e.g., isochrones), where the activation times for a 160 ms period of time are color-coded from red ("R") at about 0 ms to blue ("B") at about 160 ms. Other labeled colors on the scale between blue and red are light blue ("LB"), green ("G"), yellow ("Y"), and orange ("O"). FIG. 6B shows that the AF source moves (precesses) in a small region 600 shown by the locus of migration in FIG. 6A.

Figure 6C:
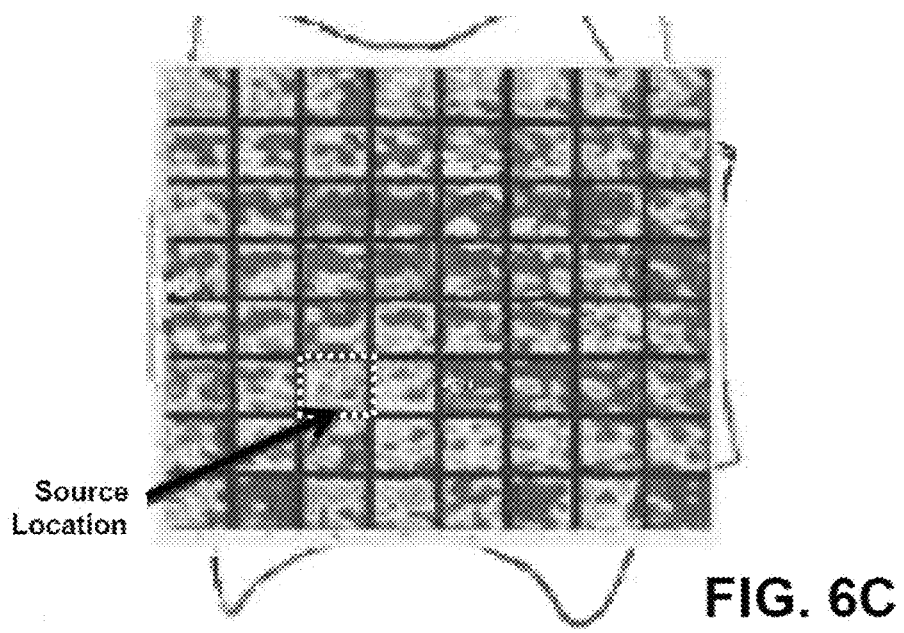
Figure 6D:
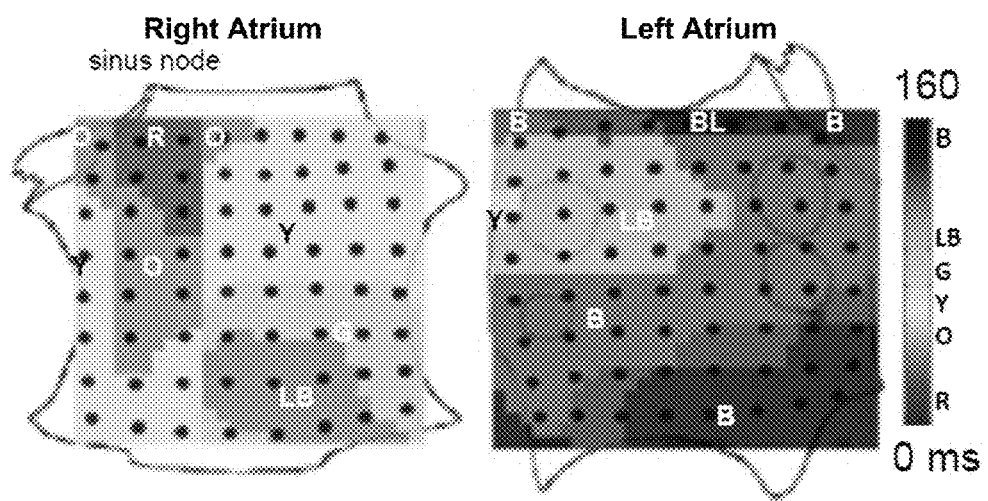
Figure 6E:
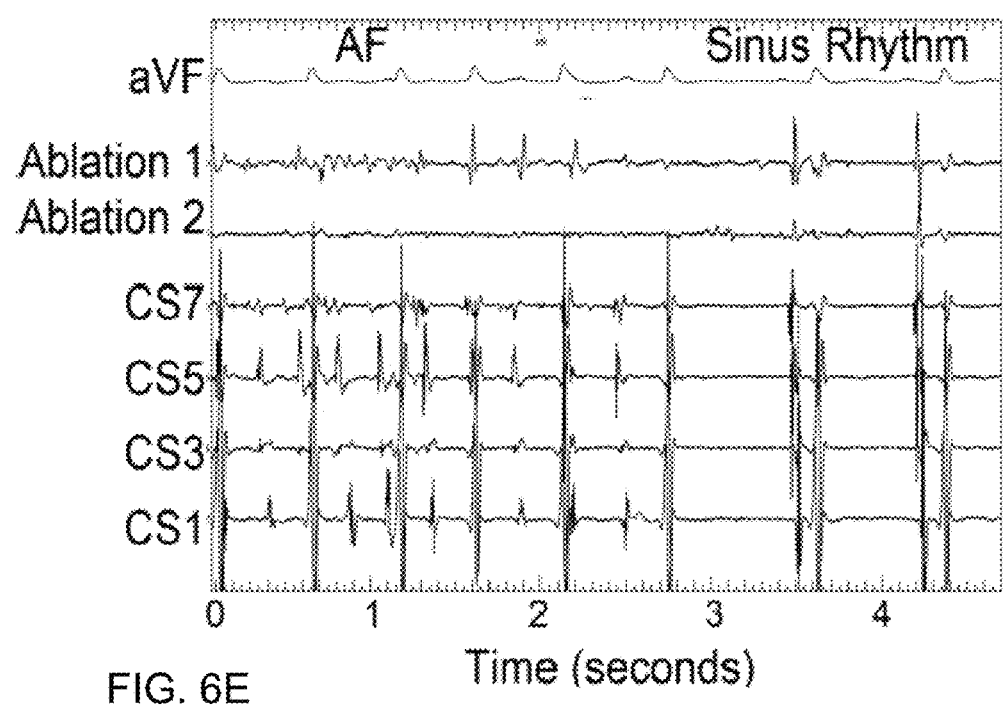

In FIG. 6C, coefficients of variability (indexes of regularity) illustrate a region of low regularity (cool colors, within the white dashed square, indicated by an arrow) relative to and surrounded by adjacent regions of high regularity (warmer colors). This region is a source of the AF and agrees precisely with the rotational source 600 in FIG. 6A. As shown on patient specific geometry in FIG. 6C, the source for AF is in the low left atrium. In FIG. 6D, electrode signals are shown during AF with termination to sinus rhythm by <1 minute after ablation at the region of high regularity around the region of low variability or high regularity (i.e., rotational source 600 in FIG. 6A), (ECG lead a VF, and electrodes at ablation catheter, coronary sinus). In FIG. 6E, an isochronal map of the sinus rhythm is shown for the referenced patient. This patient remains free of AF on implanted cardiac monitor. (Scale Bar =1cm).

FIG. 7 illustrates an example plot of indexes of regularity to identify a source of heart rhythm disorder.

The example plot of coefficients of variability (indexes of regularity) for each signal processed can be generated as a grid of sub-plots, with each sub-plot showing the coefficient of variability (index of regularity) using a different first (analysis) signal and every second (reference) signal processed against the first signal. Thereafter, the example plot can be generated as a combination of sub-plots. The example plot arranges each signal in an approximate spatial relationship with the other signals. A color is assigned to a pixel at each sensor location representing a value of the coefficient of variability (index of regularity) for the signal pair. For example, lower coefficient of variability (higher index of regularity) can be coded in red colors, while higher coefficient of variability (lower index of regularity) can be coded in blue colors. Each first (analysis) signal's sub-plot can then be placed into the larger example plot that represents that first signal's spatial location with the other processed first (analysis) signals, creating an 8×8 plot as shown in FIG. 7.

As shown in FIG. 7, a region of high regularity (warm colors, indicated by the solid white square) that surrounds an adjacent region of low regularity (cool colors, indicated by the dashed white square) can be determined. The black arrow indicates a site of successful ablation on or within the region of high regularity. Similarly, a region of low regularity that is surrounded by a region of high regularity can also be determined for ablation to eliminate the source of the cardiac rhythm disorder.

Figure 8:
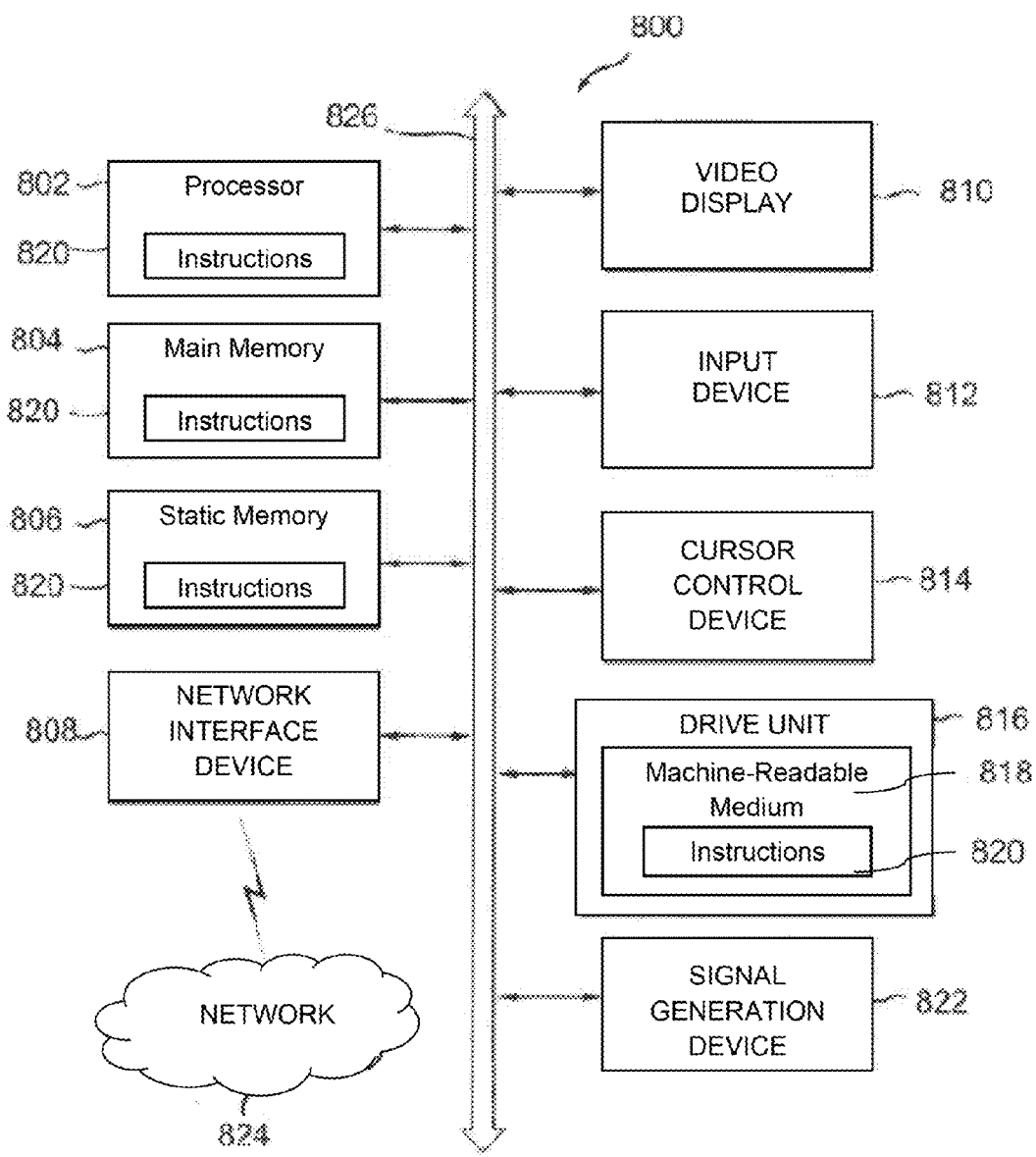
FIG. 8 is a block diagram of an illustrative embodiment of a general computer system.

FIG. 8 is a block diagram of an illustrative embodiment of a general computer system 800. The computer system 800 can be the signal processing device 114 and the computing device 116 of FIG. 1. The computer system 800 can include a set of instructions that can be executed to cause the computer system 800 to perform any one or more of the methods or computer based functions disclosed herein. The computer system 800, or any portion thereof, may operate as a standalone device or may be connected, e.g., using a network or other connection, to other computer systems or peripheral devices. For example, the computer system 800 may be operatively connected to signal processing device 114 and analysis database 118.

In operation as described in FIGS. 1-7, the identification of source(s) of heart rhythm disorders as described herein can be used to identify patients in whom therapy can be effective and to assist in guiding such therapy, which can include delivery of one or more of ablation, electrical energy, mechanical energy, drugs, cells, genes and biological agents to at least a portion of the identified source(s) of the heart.

The computer system 800 may also be implemented as or incorporated into various devices, such as a personal computer (PC), a tablet PC, a personal digital assistant (PDA), a mobile device, a palmtop computer, a laptop computer, a desktop computer, a communications device, a control system, a web appliance, or any other machine capable of executing a set of instructions (sequentially or otherwise) that specify actions to be taken by that machine. Further, while a single computer system 800 is illustrated, the term "system" shall also be taken to include any collection of systems or sub-systems that individually or jointly execute a set, or multiple sets, of instructions to perform one or more computer functions.

As illustrated in FIG. 8, the computer system 800 may include a processor 802, e.g., a central processing unit (CPU), a graphics-processing unit (GPU), or both. Moreover, the computer system 800 may include a main memory 804 and a static memory 806 that can communicate with each other via a bus 826. As shown, the computer system 800 may further include a video display unit 810, such as a liquid crystal display (LCD), an organic light emitting diode (OLED), a flat panel display, a solid state display, or a cathode ray tube (CRT). Additionally, the computer system 800 may include an input device 812, such as a keyboard, and a cursor control device 814, such as a mouse. The computer system 800 can also include a disk drive unit 816, a signal generation device 822, such as a speaker or remote control, and a network interface device 808.

In a particular embodiment, as depicted in FIG. 8, the disk drive unit 816 may include a computer-readable medium 818 in which one or more sets of instructions 820, e.g., software, can be embedded. Further, the instructions 820 may embody one or more of the methods or logic as described herein. In a particular embodiment, the instructions 820 may reside completely, or at least partially, within the main memory 804, the static memory 806, and/or within the processor 802 during execution by the computer system 800. The main memory 804 and the processor 802 also may include computer-readable media.

In an alternative embodiment, dedicated hardware implementations, such as application specific integrated circuits, programmable logic arrays and other hardware devices, can be constructed to implement one or more of the methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

In accordance with various embodiments, the methods described herein may be implemented by software programs tangibly embodied in a processor-readable medium and may be executed by a processor. Further, in an exemplary, non-limited embodiment, implementations can include distributed processing, component/object distributed processing, and parallel processing. Alternatively, virtual computer system processing can be constructed to implement one or more of the methods or functionality as described herein.

It is also contemplated that a computer-readable medium includes instructions 820 or receives and executes instructions 820 responsive to a propagated signal, so that a device connected to a network 824 can communicate voice, video or data over the network 824. Further, the instructions 820 may be transmitted or received over the network 824 via the network interface device 808.

While the computer-readable medium is shown to be a single medium, the term "computer-readable medium" includes a single medium or multiple media, such as a centralized or distributed database, and/or associated caches and servers that store one or more sets of instructions. The term "computer-readable medium" shall also include any medium that is capable of storing, encoding or carrying a set of instructions for execution by a processor or that cause a computer system to perform any one or more of the methods or operations disclosed herein.

In a particular non-limiting, example embodiment, the computer-readable medium can include a solid-state memory, such as a memory card or other package, which houses one or more non-volatile read-only memories. Further, the computer-readable medium can be a random access memory or other volatile re-writable memory. Additionally, the computer-readable medium can include a magneto-optical or optical medium, such as a disk or tapes or other storage device to capture carrier wave signals, such as a signal communicated over a transmission medium. A digital file attachment to an e-mail or other self-contained information archive or set of archives may be considered a distribution medium that is equivalent to a tangible storage medium. Accordingly, any one or more of a computer-readable medium or a distribution medium and other equivalents and successor media, in which data or instructions may be stored, are included herein.

In accordance with various embodiments, the methods described herein may be implemented as one or more software programs running on a computer processor. Dedicated hardware implementations including, but not limited to, application specific integrated circuits, programmable logic arrays, and other hardware devices can likewise be constructed to implement the methods described herein. Furthermore, alternative software implementations including, but not limited to, distributed processing or component/object distributed processing, parallel processing, or virtual machine processing can also be constructed to implement the methods described herein.

It should also be noted that software that implements the disclosed methods may optionally be stored on a tangible storage medium, such as: a magnetic medium, such as a disk or tape; a magneto-optical or optical medium, such as a disk; or a solid state medium, such as a memory card or other package that houses one or more read-only (non-volatile) memories, random access memories, or other re-writable (volatile) memories. The software may also utilize a signal containing computer instructions. A digital file attachment to e-mail or other self-contained information archive or set of archives is considered a distribution medium equivalent to a tangible storage medium. Accordingly, a tangible storage medium or distribution medium as listed herein, and other equivalents and successor media, in which the software implementations herein may be stored, are included herein.

Thus, a system and method to identify a source (or sources) of a biological rhythm disorder have been described. Although specific example embodiments have been described, it will be evident that various modifications and changes may be made to these embodiments without departing from the broader scope of the invention. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of any of the above-described embodiments, and other embodiments not specifically described herein, may be used and are fully contemplated herein.

The Abstract is provided to comply with 37 C.F.R. §1.72(b) and will allow the reader to quickly ascertain the nature and gist of the technical disclosure. It is submitted with the understanding that it will not be used to interpret or limit the scope or meaning of the claims.

In the foregoing description of the embodiments, various features are grouped together in a single embodiment for the purpose of streamlining the disclosure. This method of disclosure is not to be interpreted as reflecting that the claimed embodiments have more features than are expressly recited in each claim. Rather, as the following claims reflect, inventive subject matter lies in less than all features of a single disclosed embodiment. Thus the following claims are hereby incorporated into the Description of the Embodiments, with each claim standing on its own as a separate example embodiment.

The invention claimed is:

1. A method of locating a source of a rhythm disorder of a heart, the method comprising:
processing a first pair of cardiac signals to define a first coefficient of variability associated with a variability of the first pair of signals at a first region of the heart;
processing a second pair of cardiac signals to define a second coefficient of variability associated with a variability of the second pair of signals at a second region of the heart; and comparing the first coefficient of variability to the second coefficient of variability; and determining a direction towards the source of the rhythm disorder based on the comparison.

2. The method of claim 1, wherein processing the first pair of cardiac signals comprises processing a first cardiac signal at one or more first time points against a second cardiac signal at one or more second time points to define the first coefficient of variability based on one or more coordinate pairs of the first cardiac signal against the second cardiac signal.

3. The method of claim 1, wherein processing the second pair of cardiac signals comprises processing a third cardiac signal at one or more third time points against a fourth cardiac signal at one or more fourth time points to define the second coefficient of variability based on one or more coordinate pairs of the third cardiac signal against the fourth cardiac signal.

4. The method of claim 1, wherein the first cardiac signal and the third cardiac signal comprise a common signal.

5. The method of claim 1, wherein the first and second regions are the same region of the heart.

6. The method of claim 1, wherein the first and second regions are different regions of the heart.

7. The method of claim 1, wherein at least one of the first coefficient of variability and the second coefficient of variability is determined from at least one of a variability in signal timing and a variability in signal amplitude among at least one of the first pair of cardiac signals and the second pair of cardiac signals.

8. The method of claim 1, wherein at least one of the first coefficient of variability and the second coefficient of variability is determined from variability in signal shape among at least one of the first pair of cardiac signals and the second pair of cardiac signals.

9. The method of claim 1, wherein at least one of the first coefficient of variability and the second coefficient of variability is determined by one or more methods selected from a group consisting of standard deviation analysis, frequency analysis, entropy analysis, cross-correlation analysis, randomness analysis, Monte Carlo simulation methods, quantification of chaos, other complex statistical analyses, and combinations thereof.

10. The method of claim 1, wherein the variability is in one or more of amplitude, voltage, motion, direction, impedance, conductance, and another dimension other than time.

11. The method of claim 1, wherein the variability is in time.

12. The method of claim 1, wherein the method further comprises:

iteratively selecting the first pair of cardiac signals and the second pair of cardiac signals from a plurality of cardiac signals, each iteratively selected pair differing in at least one cardiac signal;

processing the first iteratively selected signal and the second iteratively selected signal from each pair for each iteration to define the first coefficient of variability and the second coefficient of variability, respectively;

constructing a matrix of coefficients associated with variability for the iteratively selected pairs of cardiac signals; and determining one or more sources of the rhythm disorder using the matrix of coefficients.

13. The method of claim 12, wherein determining the one or more sources comprises:

identifying from the matrix one or more regions of the heart associated with higher coefficients of variability surrounded by regions of lower coefficients of variability.

14. The system of claim 12, wherein the at least one computing device is further configured to identify from the matrix one or more regions of the heart associated with higher coefficients of variability surrounded by regions of lower coefficients of variability to determine one or more sources of the rhythm disorder.

15. The method of claim 1, wherein the source of the rhythm disorder is located in a direction from lower coefficients of variability towards higher coefficients of variability.

16. A method of locating a source of a rhythm disorder of a heart, the method comprising:

processing a first cardiac signal at one or more first time points against a second cardiac signal at one or more second time points to define a first coefficient associated with variability of one or more coordinate pairs of the first cardiac signal against the second cardiac signal;

processing a third cardiac signal at one or more third time points against a fourth cardiac signal at one or more fourth time points to define a second coefficient associated with variability of one or more coordinate pairs of the third cardiac signal against the fourth cardiac signal; and determining a direction towards the source of the rhythm disorder being from a lower coefficient of variability to a higher coefficient of variability.

17. The method of claim 16, wherein at least one of the first coefficient of variability and the second coefficient of variability is determined from at least one of variability in signal timing and a variability in signal amplitude.

18. The method of claim 16, wherein at least one of the first coefficient of variability and the second coefficient of variability is determined from variability in signal shape.

19. The method of claim 16, wherein at least one of the first coefficient of variability and the second coefficient of variability is determined by standard deviation analysis, frequency analysis, entropy analysis, cross-correlation analysis, randomness analysis, Monte Carlo simulation methods, quantification of chaos, other complex statistical analyses, and combinations thereof.

20. The method of claim 16, wherein the variability is in one or more of amplitude, voltage, motion, direction, impedance, conductance, and another dimension other than time.

21. The method of claim 16, wherein the variability is in time.

22. The method of claim 16, wherein the first cardiac signal and the second cardiac signal occur at the same points in time.

23. The method of claim 16, wherein the third cardiac signal and the fourth cardiac signal occur at the same points in time.

24. The method of claim 16, wherein the first cardiac signal and the second cardiac signal represent a first voltage time series and a second voltage time series, respectively.

25. The method of claim 16, wherein processing of cardiac signals further comprises taking derivatives of the cardiac signals, the derivatives being one of a zero order derivative and a higher order derivative.

26. The method of claim 16, wherein the first coefficient of variability is determined by a transformation of the plurality of coordinate pairs of the first cardiac signal to the plurality of coordinate pairs of the second cardiac signal.

27. The method of claim 16, wherein the second coefficient of variability is determined by a transformation of the plurality of coordinate pairs of the third cardiac signal to the plurality of coordinate pairs of the fourth cardiac signal.

28. A system to locate a source of a rhythm disorder of a heart, the system comprising at least one computing device configured to:

process a first pair of cardiac signals to define a first coefficient of variability associated with a variability of the first pair of signals at a first region of the heart;

process a second pair of cardiac signals to define a second coefficient of variability associated with a variability of the second pair of signals at a second region of the heart; and compare the first coefficient of variability to the second coefficient of variability to determine a direction towards the source of the rhythm disorder.

29. The system of claim 28, wherein the at least one computing device is configured to processes a first cardiac signal at one or more first time points against a second cardiac signal at one or more second time points to define the first coefficient of variability based on one or more coordinate pairs of the first cardiac signal against the second cardiac signal.

30. The system of claim 28, wherein the at least one computing device is configured to processes a third cardiac signal at one or more third time points against a fourth cardiac signal at one or more fourth time points to define the second coefficient of variability based on one or more coordinate pairs of the third cardiac signal against the fourth cardiac signal.

31. The system of claim 28, wherein the first cardiac signal and the third cardiac signal comprise a common signal.

32. The system of claim 28, wherein the first and second regions are the same region of the heart.

33. The system of claim 28, wherein the first and second regions are different regions of the heart.

34. The system of claim 28, wherein at least one of the first coefficient of variability and the second coefficient of variability is determined from at least one of variability in signal timing and variability in signal amplitude among at least one of the first pair of cardiac signals and the second pair of cardiac signals.

35. The system of claim 28, wherein at least one of the first coefficient of variability and the second coefficient of variability is determined from variability in signal shape among at least one of the first pair of cardiac signals and the second pair of cardiac signals.

36. The system of claim 28, wherein at least one of the first coefficient of variability and the second coefficient of variability is determined by one or more methods selected from a group consisting of standard deviation analysis, frequency analysis, entropy analysis, cross-correlation analysis, randomness analysis, Monte Carlo simulation methods, quantification of chaos, other complex statistical analyses, and combinations thereof.

37. The system of claim 28, wherein the variability is in one or more of amplitude, voltage, motion, direction, impedance, conductance, and another dimension other than time.

38. The system of claim 28, wherein the variability is in time.

39. The system of claim 28, wherein the at least one computing device is configured to:
iteratively select the first pair of cardiac signals and the second pair of cardiac signals from a plurality of cardiac signals, each iteratively selected pair differing in at least one cardiac signal;
process the first iteratively selected signal and the second iteratively selected signal from each pair for each iteration to define the first coefficient of variability and the second coefficient of variability, respectively;
construct a matrix of coefficients associated with variability for the iteratively selected pairs of cardiac signals; and
determine one or more sources of the rhythm disorder using the matrix of coefficients.

40. The system of claim 28, wherein the source of the rhythm disorder is located in a direction from lower coefficients of variability towards higher coefficients of variability.

41. A system to locate a source of a rhythm disorder of a heart, the system comprising at least one computing device configured to:
process a first cardiac signal at one or more first time points against a second cardiac signal at one or more second time points to define a first coefficient associated with variability of one or more coordinate pairs of the first cardiac signal against the second cardiac signal;
process a third cardiac signal at one or more third time points against a fourth cardiac signal at one or more fourth time points to define a second coefficient associated with variability of one or more coordinate pairs of the third cardiac signal against the fourth cardiac signal; and
determine a direction towards the source of the rhythm disorder being from a lower coefficient of variability to a higher coefficient of variability.

42. The system of claim 41, wherein at least one of the first coefficient of variability and the second coefficient of variability is determined from at least one of variability in signal timing and a variability in signal amplitude.

43. The system of claim 41, wherein at least one of the first coefficient of variability and the second coefficient of variability is determined from variability in signal shape.

44. The method of claim 41, wherein at least one of the first coefficient of variability and the second coefficient of variability is determined by standard deviation analysis, frequency analysis, entropy analysis, cross-correlation analysis, randomness analysis, Monte Carlo simulation methods, quantification of chaos, other complex statistical analyses, and combinations thereof.

45. The system of claim 41, wherein the variability is in one or more of amplitude, voltage, motion, direction, impedance, conductance, and another dimension other than time.

46. The system of claim 41, wherein the variability is in time.

47. The system of claim 41, wherein the first cardiac signal and the second cardiac signal occur at the same points in time.

48. The system of claim 41, wherein the third cardiac signal and the fourth cardiac signal occur at the same points in time.

49. The system of claim 41, wherein the first cardiac signal and the second cardiac signal represent a first voltage time series and a second voltage time series, respectively.

50. The system of claim 41, wherein the at least one computing device is further configured to processes cardiac signals further by taking derivatives of the cardiac signals, the derivatives being one of a zero order derivative and a higher order derivative.

51. The system of claim 41, wherein the first coefficient of variability is determined by a transformation of the plurality of coordinate pairs of the first cardiac signal to the plurality of coordinate pairs of the second cardiac signal.

52. The system of claim 41, wherein the second coefficient of variability is determined by a transformation of the plurality of coordinate pairs of the third cardiac signal to the plurality of coordinate pairs of the fourth cardiac signal.

* * * * *